(12) United States Patent
Goethel et al.

(10) Patent No.: US 6,196,999 B1
(45) Date of Patent: Mar. 6, 2001

(54) SYRINGE/PLUNGER COUPLING

(75) Inventors: James H. Goethel, Cincinnati; Robert G. Bergen, West Chester, both of OH (US)

(73) Assignee: Liebel-Flarsheim Company, Cincinnati, OH (US)

( * ) Notice: Subject to any disclaimer, the term of this patent is extended or adjusted under 35 U.S.C. 154(b) by 0 days.

(21) Appl. No.: 09/245,229

(22) Filed: Feb. 5, 1999

(51) Int. Cl.[7] .......................... A61M 37/00; A61M 1/00; A61M 5/315
(52) U.S. Cl. ..................... 604/131; 604/121; 604/218
(58) Field of Search ................... 604/118, 121, 604/131, 154, 155, 218

(56) References Cited

U.S. PATENT DOCUMENTS

| | | | |
|---|---|---|---|
| 4,677,980 | 7/1987 | Reilly et al. | 128/655 |
| 4,738,664 | 4/1988 | Prindle | 604/228 |
| 4,911,695 | 3/1990 | Lindner | 604/228 |
| 5,004,460 | 4/1991 | Gimeno | 604/228 |
| 5,007,904 | 4/1991 | Densmore et al. | 604/228 |
| 5,269,762 | 12/1993 | Armbruster et al. | 604/155 |
| 5,279,569 | 1/1994 | Neer et al. | 604/154 |
| 5,322,511 | 6/1994 | Armbruster et al. | 604/155 |
| 5,484,414 | 1/1996 | Pace | 604/110 |
| 5,535,746 | 7/1996 | Hoover et al. | 128/655 |
| 5,658,261 | 8/1997 | Neer et al. | 604/240 |
| 5,865,805 | 2/1999 | Ziemba | 604/154 |
| 5,868,710 | 2/1999 | Battiato et al. | 604/123 |

FOREIGN PATENT DOCUMENTS

| | | |
|---|---|---|
| 0 709 106 A2 | 1/1996 | (EP) . |
| 0 709 106 A3 | 11/1996 | (EP) . |

*Primary Examiner*—Sharon Kennedy
*Assistant Examiner*—Michael J. Hayes
(74) *Attorney, Agent, or Firm*—Wood, Herron & Evans, L.L.P.

(57) ABSTRACT

A medical fluid injector, replaceable syringe, and coupling mechanism to engage the syringe plunger to the plunger drive ram of the injector are provided wherein coupling involves a cam cleat-like mechanism, thereby allowing for cooperative movement between the plunger drive ram and syringe plunger. The coupling mechanism of the plunger drive ram is provided with first and second movable members, each having toothed, arcuate surfaces, while the coupling mechanism of the syringe plunger is provided with a knurled extension. Disengagement of the coupling mechanism is facilitated by translational movement of a face plate located on the forward end of the injector housing.

11 Claims, 4 Drawing Sheets

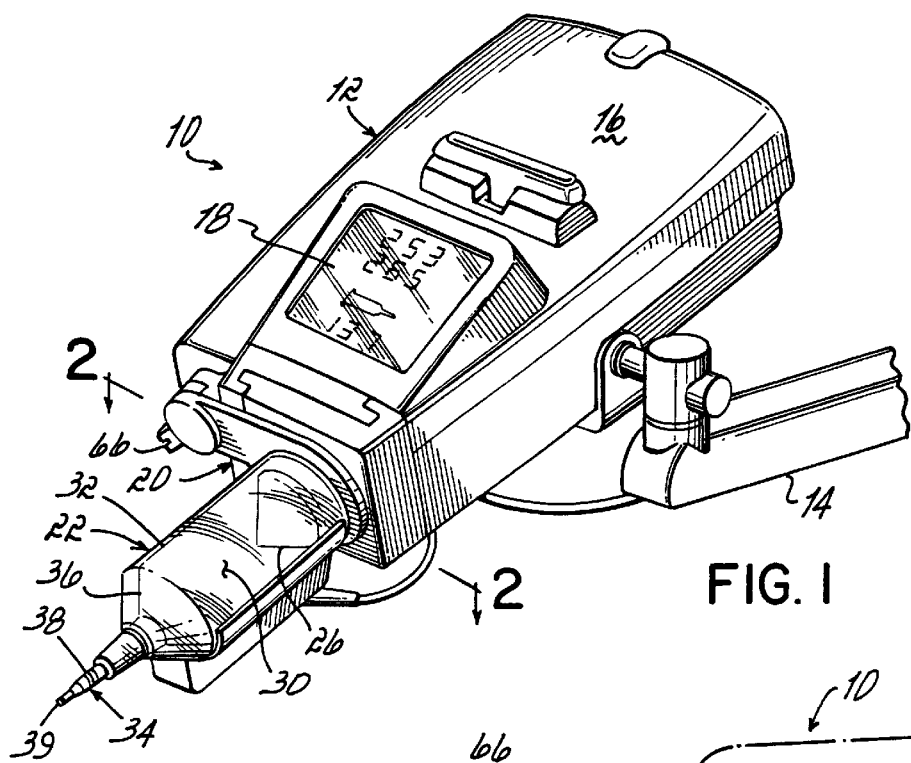
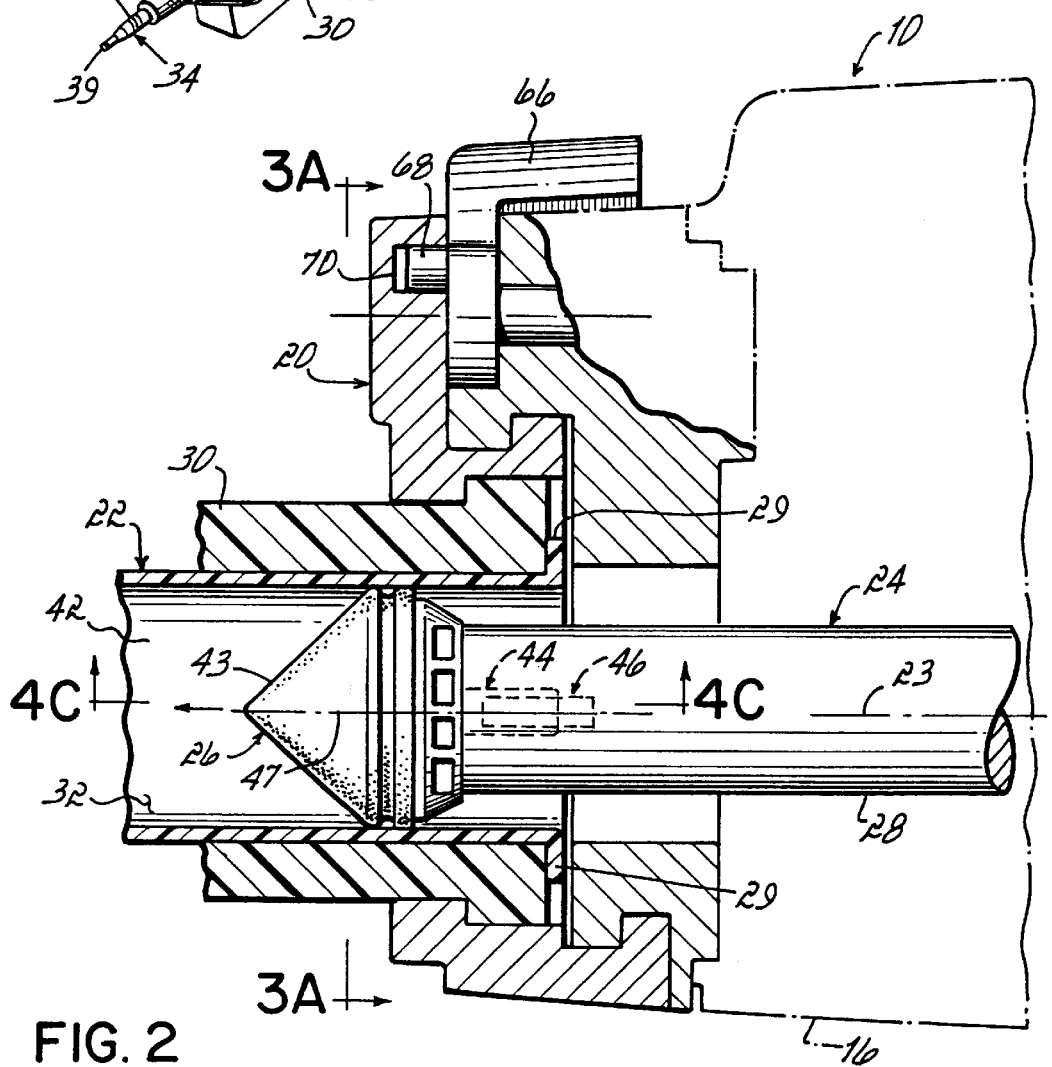
FIG. 1
FIG. 2

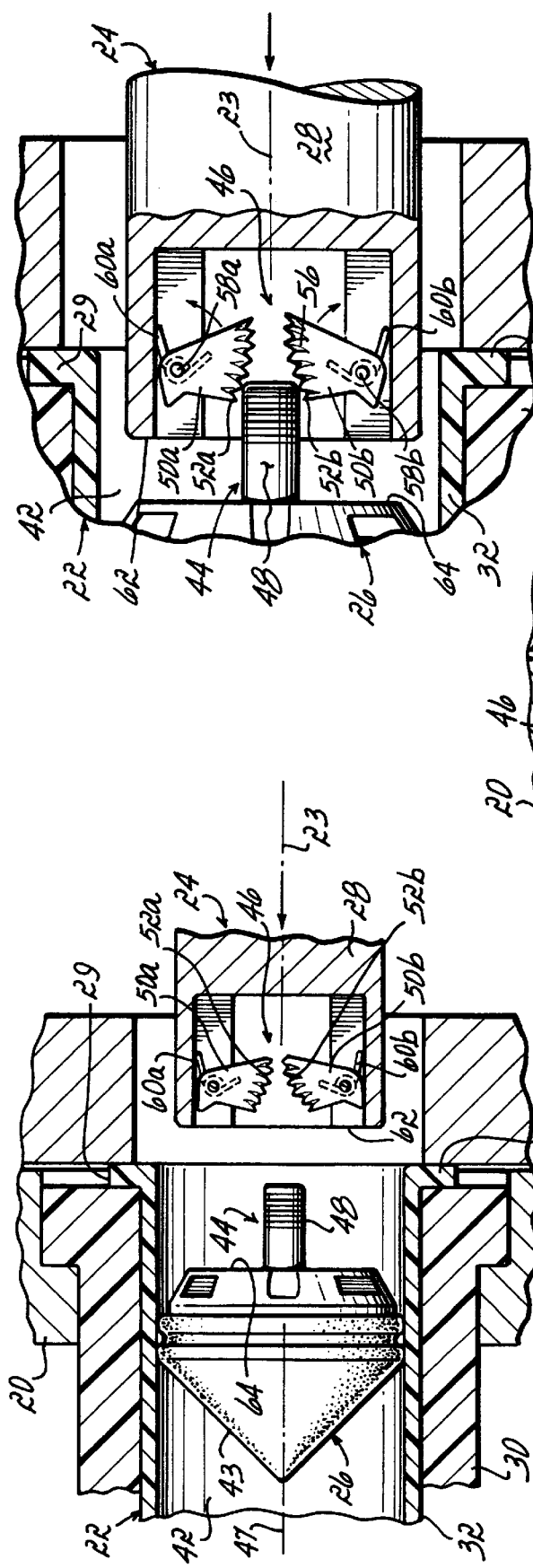
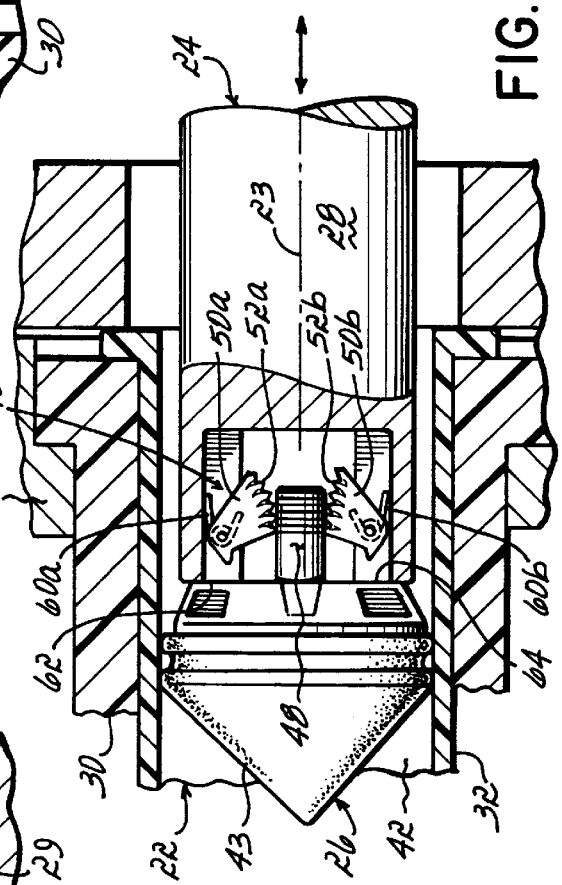
FIG. 4A
FIG. 4B
FIG. 4C

SYRINGE/PLUNGER COUPLING

FIELD OF THE INVENTION

The present invention relates to injectors for injecting fluid into animals.

BACKGROUND OF THE INVENTION

During many medical procedures, various fluids are injected into patients for purposes of diagnosis or treatment. An example of one such fluid is contrast media used to enhance angiography or CT imaging. The injectors used in these procedures are automated devices that expel the fluid from a syringe, through a tube, and into the subject.

Injectors suitable for these applications must have relatively large volume syringes and be capable of producing relatively large flow rates and injection pressures. For this reason, injectors for such applications typically include large, high mass injector motors and drive t rains. These are typically housed in an injection head, which is supported by a floor, wall, or ceiling mounted arm.

In many such injectors the syringes are replaceable. In one exemplary injector, to replace the syringe, a front face plate which facilitates coupling between the syringe plunger and the plunger drive ram is moved, the used syringe detached, and a fresh syringe attached.

When a used syringe is removed, a replacement syringe is installed on the injector. The rearward face of the syringe plunger has a coupling element referred to as a button. This button is mushroom-shaped and consists of an extension protruding from the rearward face of the syringe plunger, topped by a cap. When the new syringe plunger is inserted, the button contacts the plunger coupling engagement jaws located on the forward end of the plunger drive ram. These jaws then snap around the button of the syringe plunger, thereby connecting the syringe plunger to the plunger drive ram.

This "jaw and button" coupling mechanism in an injector does not result in a perfect fit between the jaws on the plunger drive ram and the button on the rearward face of the syringe plunger. The ends of the jaws are not completely snug around the cap of the button on the rearward face of the syringe plunger. This results in some amount of "backlash" between the mating sections of the coupling mechanisms. Due to this spacing the syringe plunger does not move cooperatively with the plunger drive ram upon motorized, automated movement of the plunger drive ram. Rather, the jaw and button embodiment features an initial movement of the plunger drive ram and a subsequent responsive movement of the syringe plunger. Thus, there is an element of lag time, albeit small, in deploying the syringe plunger to inject fluids to a subject. This is an unfortunate problem because many medical applications require an extremely high degree of accuracy, especially in the timing and volume of substances injected into the body. The lag time inherent in the jaw and button arrangement creates a reduced degree of accuracy.

Accordingly, to improve accuracy, there is a need for a coupling mechanism for the syringe plunger and plunger drive ram where movement of the syringe plunger is directly cooperative with movement of the plunger drive ram, allowing for enhanced accuracy in the volume of a fluid injected into a subject.

SUMMARY OF THE INVENTION

It is an objective of the present invention to provide an apparatus which allows for increased accuracy in the injection of fluids into human or other animal subjects. In accordance with this objective, improvements are made on the syringe plunger/plunger drive ram coupling mechanisms of the typical injector using replacement syringe plungers.

In particular, an injector in accordance with the invention features a new method for engaging the syringe plunger allowing for increased accuracy due to its tight, backlash-free grip. As opposed to the use of the jaw and button coupling arrangement in the prior art, the coupling mechanism of the present invention is a cam cleat. This cam cleat coupling mechanism creates a tight grip between the mating elements of the syringe plunger and plunger drive ram, thereby reducing lag time between movement of the plunger drive ram and the syringe plunger. Thus, the syringe plunger moves cooperatively with the plunger drive ram whether extending or retracting. This results in increased accuracy in the volume of fluid injected into a subject and aids in the efficient removal of air from the syringe.

In one specific disclosed embodiment, the coupling mechanism located on the end of the plunger drive ram that engages the syringe plunger is an inwardly facing pair of jaws forming the cam cleat. This cam cleat engages a cylindrical extension located on the rearwardly facing surface of the syringe plunger. This cylindrical extension is generally knurled. The cylindrical extension is centrally located and protrudes along the longitudinal axis of the syringe plunger parallel to the direction of the plunger's movement. The cam cleat structure on the forward end of the plunger drive ram forms a connection between the syringe plunger and plunger drive ram when it is engaged by the cylindrical extension, during insertion of the syringe plunger into the syringe. As the motorized drive shaft moves the plunger drive ram forward into contact with the syringe plunger, the two pawls of the cam cleat rotate away from the cylindrical extension while still remaining in contact with it. The toothed faces of the pawls grip onto the knurled extension protruding from the syringe plunger. Each pawl of the cam cleat contains a tension spring so that although the cylindrical extension can be freely inserted to the pawls of the cam cleat, it cannot be removed by longitudinal motion due to the grip of the cam cleat. Thus, once coupled, the mechanism remains engaged during longitudinal motion of the drive to cause the syringe plunger to cooperatively move forward or backward with the plunger drive ram.

In alternate embodiments of the invention, the extension protruding rearwardly from the syringe plunger need not be cylindrical, i.e., circular in cross-section. It may have a rectangular, oval, football-like, or any other cross-sectional shape amenable to insertion between the two pawls of the cam cleat coupling mechanism.

Disengagement of the syringe plunger from the plunger drive ram occurs by relative movement of the syringe plunger in a direction perpendicular to the motion of the plunger drive ram. By this movement, the cylindrical extension on the rearward face of the syringe plunger is pulled away from the pawls of the cam cleat. In the specific disclosed embodiment, this disengagement occurs by movement of a face plate located between the pressure jacket of the injector and the injector housing. In other embodiments, an asymmetrical coupling is provided that engages and disengages the syringe plunger upon rotational movement of the syringe with respect to the drive.

The above and other objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIG. 1 is a perspective view of an injector embodying principles of the present invention.

FIG. 2 is a cross-sectional view along lines 2—2 of FIG. 1 illustrating a replaceable syringe plunger engaged with the plunger drive ram of the injector within the syringe cavity.

FIG. 4A illustrates the coupling mechanism of the plunger drive ram disengaged from the coupling element of the syringe plunger.

FIG. 4B illustrates the coupling mechanism of the plunger drive ram longitudinally moving into engagement with the coupling element of the syringe plunger.

FIG. 4C is a cross-sectional view along lines 4C—4C of FIG. 2 illustrating the coupling mechanism of the plunger drive ram in engagement with the coupling element of the syringe plunger.

DETAILED DESCRIPTION OF SPECIFIC EMBODIMENTS

Figure 3A:
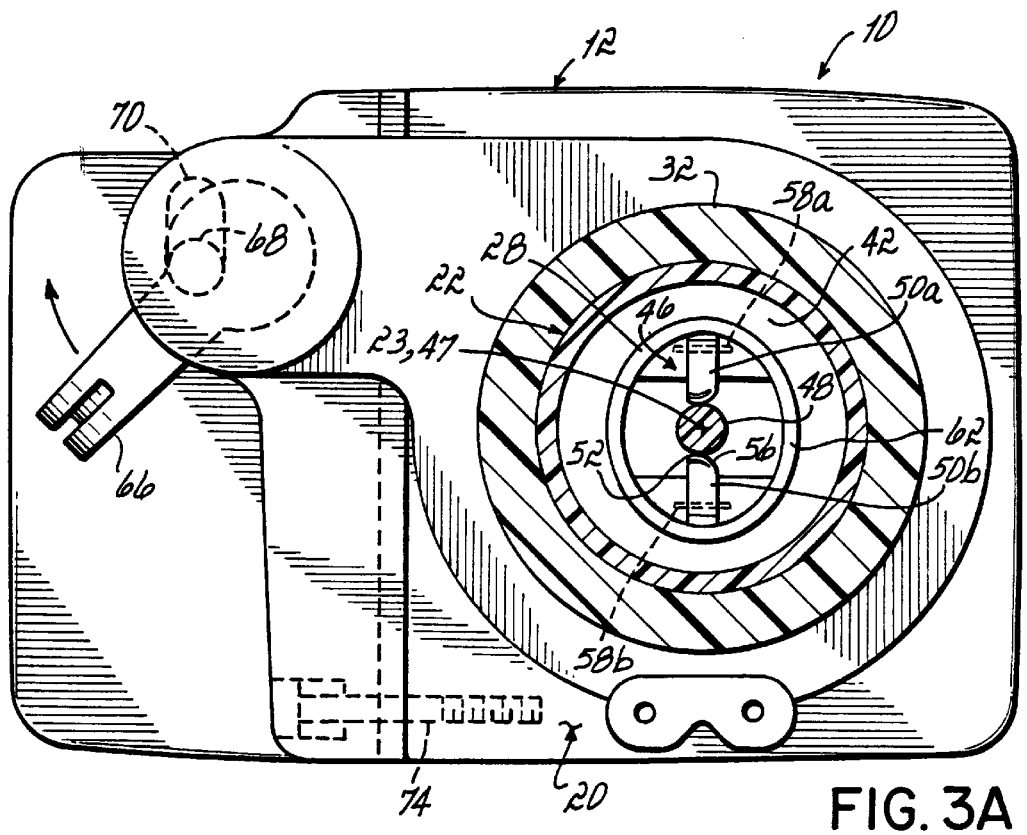
FIG. 3A is a cross-sectional view along lines 3A—3A of FIG. 2 illustrating the face plate of the injector in its locked position and showing the engagement of the coupling mechanisms of the syringe plunger and plunger drive ram.

Referring to FIG. 1, the injector head 12 is depicted attached to an arm 14, which in turn may be mounted to a ceiling, wall or floor joint. This allows motion of the injector head 12 that it may be positioned to load the syringe 22 and to inject fluids into an animal subject. Surrounding the inner mechanism of the injector 10 is the injector housing 16. This housing includes a display panel 18. The display panel 18 aids the operator of the injector 10 in monitoring amounts of fluid injected into an animal subject.

On the forward end of the injector housing 16, positioned between the injector 10 and the syringe 22, is a face plate 20. This face plate 20 is slidable along a plane perpendicular to the longitudinal axis 23 of the motion of the drive shaft 24 of the injector 10. The purpose of this face plate 20 is to facilitate connection between the injector housing 16 and the syringe 22, and to facilitate disengagement of a coupling element 44 of a syringe plunger 26 from a coupling mechanism 46 of a plunger drive ram 28 as best shown in FIGS. 2–4C.

A pressure jacket 30, preferably transparent, extends outwardly from the face plate 20, and houses a replaceable syringe 22. The syringe 22 and pressure jacket 30 are constructed such that they collectively withstand the injection pressures created by the injector 10 during an injection operation. The syringe 22 includes a syringe plunger 26. It should be noted that the pressure jacket is not a necessary feature of the invention, especially when applied to low pressure applications.

The syringe 22 includes an exterior cylindrical barrel or body 32, which at its forward end is integral with a conical front wall section 36. A neck 38, terminating in discharge tip 34, extends forwardly from and is integral with the front wall 36. The body 22 of the syringe snugly engages the interior walls of the pressure jacket 30. This syringe 22 includes a syringe mating section 29, preferably in the form of a radially outwardly extending annular flange, which is positioned in a plane perpendicular to the axis of and integral with the rear end of the cylindrical body of the syringe. The syringe mating section is arranged, when the syringe is located within the pressure jacket, to align with cooperating mating sections located on the rear end of the pressure jacket. In this manner, the syringe and pressure jacket mating sections facilitate the connection of the syringe 22 to the injector 10.

The neck 38 of the discharge tip 34 contains an orifice 39 in its remote end which communicates with an internal syringe cavity 42 formed within the neck 38, the conical front wall 36 and the cylindrical barrel 32 of the syringe 22. The rear end of the cavity 42 is further defined by a forward facing conical surface of the syringe plunger 26. The conical surface is of a slope which conforms to the slope of the interior of the conical front wall 36. The syringe plunger 26 is snugly slidable within the body of the syringe 22 case such that the cavity is of variable volume.

Referring now to FIG. 2, the syringe plunger 26 can be seen more clearly within the cylindrical barrel 32 of the syringe 22. The syringe plunger 26 is attached to the plunger drive ram 28 of the injector 10. The plunger drive ram 28 is driven by a motor (not shown) to deploy the plunger drive ram 28 and syringe plunger 26 in a forward or rearward motion along the axis of symmetry 23 of the syringe cavity 42 to inject fluid into an animal subject or fill the syringe with fluid, respectively. As illustrated in FIGS. 2–4C, the end of the drive ram 28 proximate to the syringe plunger 26 is provided with a cavity, open at its front, in which is positioned the coupling mechanism 46 (FIG. 4A).

FIG. 2 depicts, in engaged relationship, the coupling element 44 of the syringe plunger 26 and the coupling mechanism 46 of the plunger drive ram 28. Once the coupling mechanisms 44 and 46 are engaged, the syringe plunger 26 can be moved rearwardly by the plunger drive ram 28 under force of the injector motor when it is desired to retract the syringe plunger, such as when filling the syringe.

Figure 3B:
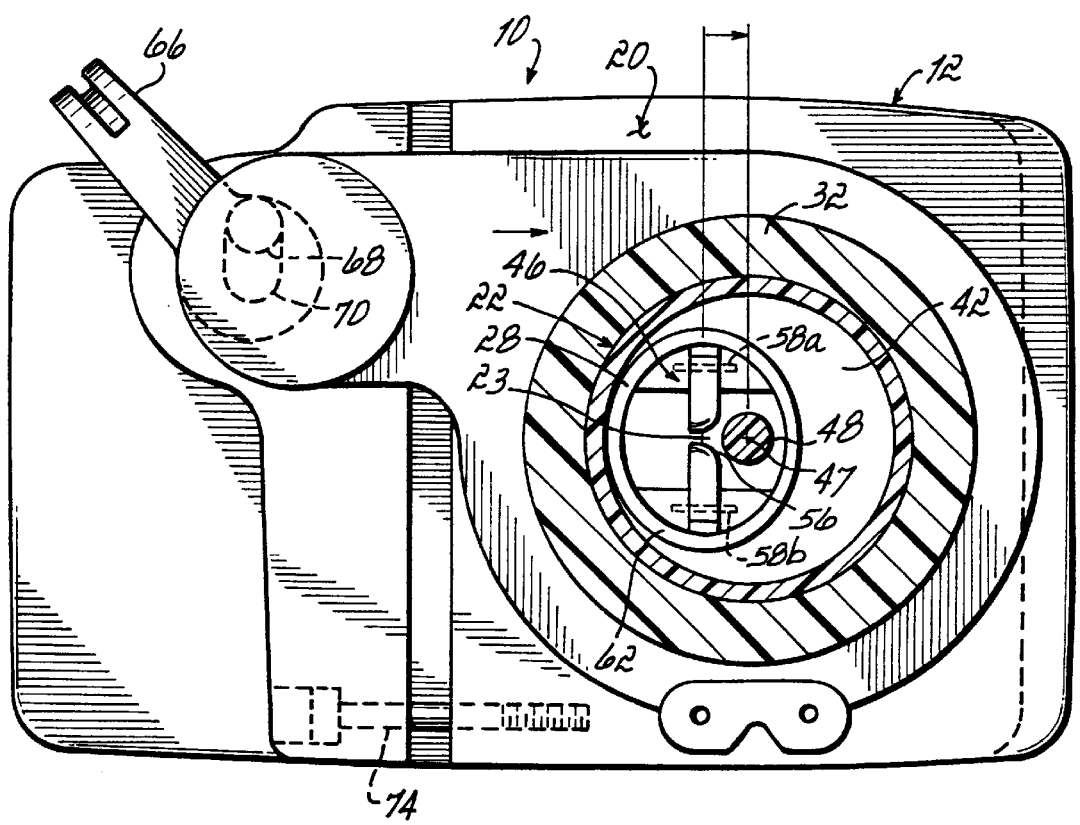
FIG. 3B illustrates the face plate of the injector in its unlocked position and shows the disengagement of the coupling element of the syringe plunger from the coupling mechanism of the plunger drive ram.

Referring now to FIGS. 2 and 3A–3B in the primary embodiment, the syringe plunger coupling element 44 is in the form of a rearwardly extending cylindrical extension 48 which is centrally located on the rearward face of the syringe plunger 26. The extension 48 is coaxial with the longitudinal axis 23 of symmetry of the drive shaft 24. In the specific disclosed embodiment, the cylindrical extension 48 is knurled to aid the grip between the coupling elements 44 and 46.

The drive ram coupling mechanism 46, located in the cavity on the forward end of the plunger drive ram 28 of the injector proximate to the syringe plunger 26, is in the nature of a dual pawl cam cleat. This coupling mechanism includes first and second pivotally movable members 50*a* and 50*b* having opposed faces, preferably arcuately shaped, each bearing a plurality of ridges of teeth 52*a* and 52*b*. The pivotal movement of members 50*a* and 50*b* alters the distance between their faces. In the specific disclosed embodiment, these first and second movable members 50*a* and 50*b* constitute two pawls of the cam cleat coupling mechanism 46. While two movable pawls are desired, it is possible to use a single movable pawl disposed in spaced relation to a nonmovable pawl-shaped stop or abutment toward which the movable pawl is biased.

Referring now the FIGS. 3A–3B and 4A–4C, the movable pawls 50*a* and 50*b* are pivotally mounted about shafts or pivot pins 58*a* and 58*b*, respectively, which pins also mount bias springs 60*a* and 60*b*. One end of each of the springs 60*a* and 60*b* is in contact with its respectively associated pawl 50*a* and 50*b,* and the opposite end of each of the springs 60*a* and 60*b* seats or bears against portions of the inner wall of the cavity of the plunger drive ram 28. The springs 60*a* and 60*b* are journaled about the pins 58*a* and 58*b* which form the pivot axes of the movable pawls 50*a* and 50*b.* The pawls 50*a* and 50*b* of the cam cleat coupling mechanism 46 are biased toward the axis of symmetry 23 of the plunger drive ram 28 by the springs 60*a* and 60*b* (FIG. 4A). Stated differently, the springs 60*a* and 60*b* bias the pawls 54 such that their confronting faces are urged toward each other. An advantage of the coupling mechanism 46 of the plunger drive ram 28 is that once the cylindrical extension 48 of the syringe coupling element 44 is inserted into the cam cleat coupling mechanism 46, it cannot be extracted by reverse longitudinal motion of the ram drive 28. As such, any reverse movement of the ram drive 28 results in intensified gripping of the syringe plunger extension 48 by the pawls 50*a* and 50*b.*

When a syringe 22 is initially positioned in the pressure jacket 30, the longitudinal axis 47 of syringe plunger extension 48 is in alignment with the longitudinal axis 23 of the drive ram 28, and the first and second pawls 50*a* and 50*b* of the coupling mechanism 46 of the drive ram 28 are axially spaced from, and in alignment with, the syringe plunger extension 48 of the syringe coupling element 44 on the rearward face of the syringe plunger 26, as best seen in FIG. 4A. Operation of the motor advances the drive ram 28 forwardly along its longitudinal axis to move the pawls 50*a* and 50*b* of coupling mechanism 46 toward and into engagement with the cylindrical extension 48 extending rearwardly from the rearward face of the syringe plunger 26. FIG. 4B depicts the advancing pawls 50*a* and 50*b* initially contacting the stationary syringe plunger extension 48, with the pawls just starting to spread apart. FIG. 4C depicts the relationship of the pawls 50*a* and 50*b* after they have been spread apart sufficiently to grip the syringe plunger extension 48 located therebetween. Ultimately, as seen in FIG. 4C, the forward end (leftmost end) 62 of drive ram 28 engages the rearward face 64 of the syringe plunger 26, so that any further forward (leftward) movement of drive ram 28 will directly result in corresponding forward movement of the syringe plunger 26. At this same time, with the pawls 50*a* and 50*b* of coupling mechanism 46 snugly embracing the syringe plunger cylindrical extension 48 under the force of the bias springs 60*a* and 60*b,* any reverse movement of the motorized drive ram 28 causes the syringe plunger 26 to be driven rearwardly (rightwardly) relative to the cylindrical barrel 32 of the syringe 22. Significantly, there is reduced "backlash" or lost motion between the syringe plunger and the drive ram upon initial rearward (rightward) movement of the drive ram relative to the syringe plunger, as compared to the jaw and button coupling arrangement of the prior art.

Figure 5A:
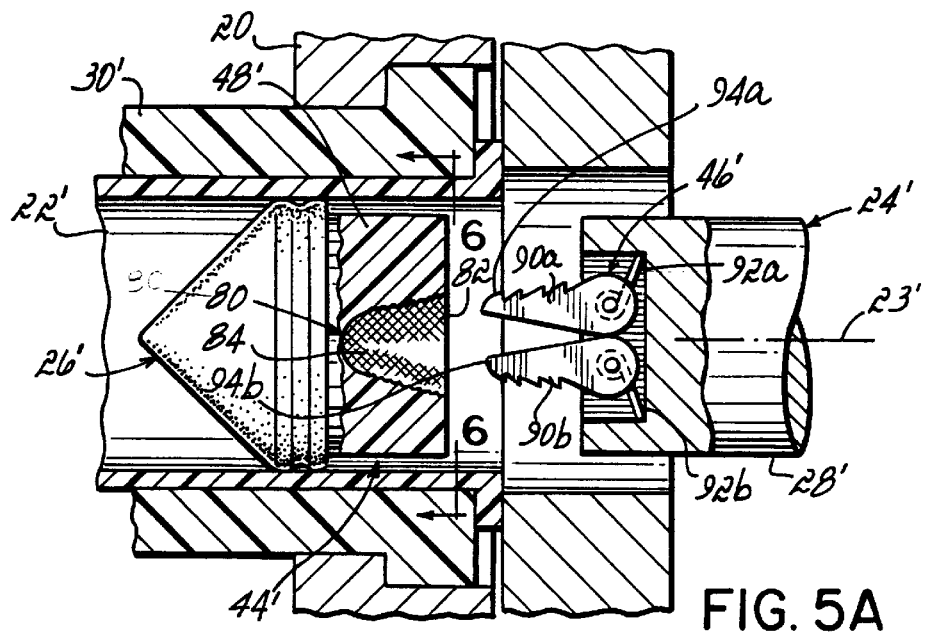
FIG. 5A illustrates an alternate embodiment of the coupling mechanism of the plunger drive ram disengaged from the coupling element of the syringe plunger.
Figure 5B:
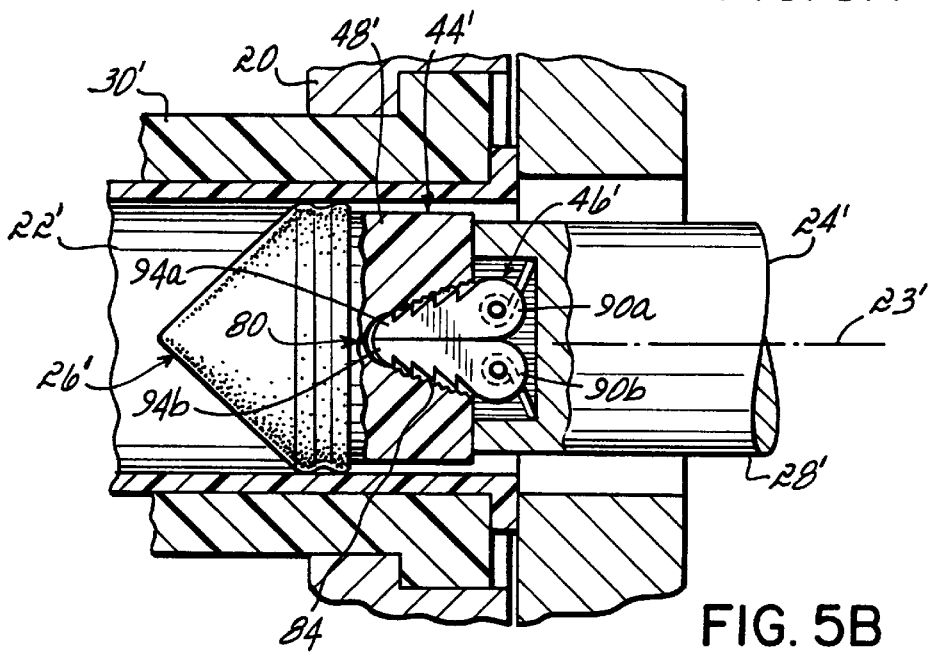
FIG. 5B illustrates the alternate embodiment of the coupling mechanism of the plunger drive ram in engagement with the coupling element of the syringe plunger.
Figure 6:
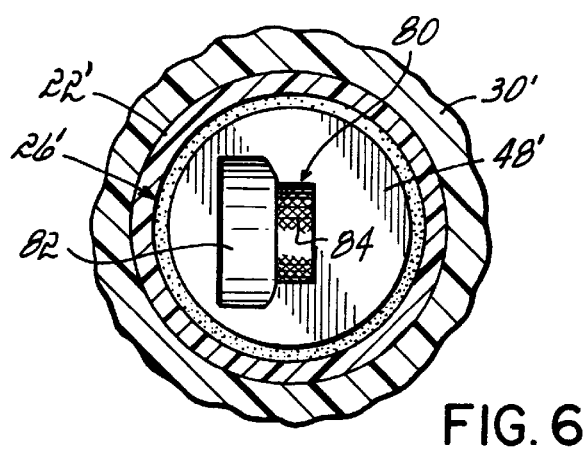
FIG. 6 illustrates the alternate embodiment of the coupling element of the syringe plunger and illustrates a "T" shaped opening.

In one alternate embodiment of the invention (as shown in FIGS. 5A, 5B, and 6) the syringe plunger coupling element 44' is in the form of a rearwardly extending cylindrical extension 48' which is centrally located on the rearward face of the syringe plunger 26'. This cylindrical extension contains an interior cavity 80, the cross-sections of which are "T" shaped. An opening 82 to this cavity 80 is located at the end of the rearward facing coupling element 44' most proximate to the drive ram 28'. The longitudinal axis of this extension 48' is coaxial with the longitudinal axis 23' of symmetry of the drive shaft 24'. The walls of the cavity 80 of the cylindrical extension 48' are knurled to aid the grip of the coupling mechanisms 44' and 46'.

Referring to FIG. 5A, depicting this alternate embodiment, the drive ram coupling mechanism 46' located in the cavity on the forward end of the plunger drive ram 28' of the injector proximate to the syringe plunger 26', is in the form of two pawls. The pawls 90*a* and 90*b* of the coupling mechanism 46' are biased away from the axis of symmetry 23' of the plunger drive ram 28' by the springs 92*a* and 92*b.*

In this alternate embodiment, when a syringe 22' is initially positioned in the pressure jacket 30', the longitudinal axis of syringe plunger extension 48' is in alignment with the longitudinal axis 23' of the drive ram 28', and the first and second pawls 90*a* and 90*b* of the coupling mechanism 46' of the drive ram 28' are axially spaced from, and in alignment with, the opening 82 of the syringe plunger extension 48' of the syringe coupling element 44' on the rearward face of the syringe plunger 26'. Operation of the motor advances the drive ram 28' forwardly along its longitudinal axis to move the pawls 90*a* and 90*b* of coupling mechanism 46' toward and into engagement with the cylindrical extension 48' extending rearwardly from the rearward face of the syringe plunger 26' (FIG. 5B). As the advancing pawls 90*a* and 90*b* initially enter the cavity 80 of plunger extension 48', the pawls 90*a* and 90*b,* which are tapered toward their forward ends 94*a* and 94*b* are forced toward one another by the walls of the cavity 80, overcoming the outward bias of springs 90*a* and 90*b.* FIG. 5B depicts the relationship of the pawls 90*a* and 90*b* after they have fully entered the cavity 80 to grip the knurled wall 84 of the cavity. Ultimately, the syringe plunger 26' and drive ram 28' will move in a cooperative motion as in the primary embodiment of the invention.

Referring now to FIGS. 3A and 3B, disengagement of the coupling mechanisms 44 and 46 from one another is facilitated through the use of a laterally movable face plate 20. The face plate 20, from which extends the pressure jacket, is located on the forward end of the injector housing 16. The face plate 20 is movable along a plane perpendicular to the longitudinal axis 23 of a syringe located in the pressure jacket and the longitudinal axis of the drive ram 28. The face plate 20 includes a mechanism to facilitate translatory motion of the face plate 20 with respect to the front of the injector housing and the longitudinal axis of the drive ram 28. In the specific disclosed embodiment, this mechanism comprises a rotatable lever 66 which is used to move the face plate 20 from a locked to an unlocked position. In its locked position, seen in FIG. 3A, the face plate 20 holds the syringe 22 so that the axis of symmetry of both the syringe cylindrical barrel 32 and syringe plunger 26 are in axial alignment with the longitudinal axis 23 of the drive ram 28. This positions the coupling mechanisms 44 and 46 of the rearward face of the syringe plunger 26 and the forward end of the plunger drive ram 28 in alignment with each other to facilitate coupling as described above and depicted in FIGS. 4A, 4B, and 4C.

Disengagement of the coupling mechanisms 44 and 46 can thereafter be achieved by translational movement of the cylindrical syringe plunger extension 48 away from the pawls 50*a* and 50*b* in a lateral direction, that is, in a transverse direction perpendicular to the longitudinal axis of the syringe plunger extension and the drive ram 28. In the specific disclosed embodiment, rotation of the face plate lever 66 from its locked to unlocked position results in a transverse translational movement of the face plate 20 along in a direction perpendicular to the longitudinal axis of the drive ram 28 of the injector 10 as seen in FIG. 3B. As this occurs, the syringe 22, which is located in the pressure jacket fixedly attached to the face plate 20 also moves in a transverse translational direction relative to the longitudinal axis of the drive ram 28. In so doing, the syringe plunger 26 moves transversely away from the plunger drive ram 28. This results in the syringe plunger extension 48 slipping out from between the pawls 50a and 50b, whereupon the cylindrical extension 48 extending from the rearward face of the syringe plunger 26 becomes disengaged from the pawls 50a and 50b of the coupling mechanism 46 located on the forward end of the plunger drive ram 28. In such a position, the syringe may be removed and the injector prepared for the insertion of a new syringe. This same method of disengagement may be used for the coupling mechanisms 44' and 46' of the alternate embodiment depicted in FIGS. 5A and 5B.

The primary embodiment of the reduced-backlash coupling invention has been described with respect to a rear, or breech, loading injector having a pressure jacket. The face plate has been described as capable of lateral movement in a direction perpendicular to the longitudinal axis of the injector drive ram to facilitate disengagement of the drive ram pawls and rearward syringe plunger extension. Such transverse face plate movement to disengage a button extending rearwardly from a syringe plunger relative to a pair of button-engaging jaws mounted on the forward end of an injector drive ram, is old and well known. Such transverse face plate motion has been used for years in rear or breech loading injectors sold by Liebel-Flarsheim Company, the assignee of the present application. Such injectors were designated Models Angiomat 3000 and 6000 and CT 9000. In addition to lateral motion, the known face plate also is capable of downward pivotal motion to enable rear loading a new syringe into the pressure jacket; and/or unloading or removing a used syringe from the pressure jacket after the face plate has been laterally moved to disengage the rearwardly extending syringe plunger button and the drive ram jaws.

The backlash-free coupling of this invention can also be used with a front loading injector of the type disclosed in U.S. Pat. No. 5,456,669 owned by Liebel-Flarsheim Company, the assignee of the present application. The disclosure of the aforesaid patent is incorporated herein in its entirety by reference.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. An injector for injecting fluids from a syringe into an animal subject comprising:
   a plunger drive ram bidirectionally movable along an axis;
   a motor drivingly coupled to said drive ram to selectively advance and retract said drive ram along said axis;
   a syringe mount engageable with a syringe to position said syringe relative to said injector to permit said drive ram to engage and move a plunger within said syringe;
   a coupling mechanism located at and movable with the forward end of said drive ram for engagement with a coupling element extending rearwardly from the plunger of a syringe engaged by said syringe mount, said coupling mechanism including first and second movable members having faces spring-biased relative to each other, which each bear a plurality of teeth, movement of said members altering the distance between said faces to permit said faces to slide along and grip the rearwardly extending coupling element of a syringe plunger upon relative advancement of said ram toward said coupling element and to retract the syringe plunger with reduced lost motion therebetween upon initiation of relative rearward movement of the drive ram with respect to the syringe plunger; and
   a control circuit controlling said motor to selectively bidirectionally advance and retract said drive ram and syringe plunger to transfer fluid from and to said syringe respectively.

2. The injector of claim 1 wherein first and second biased movable members are pivotable toward and away from each other.

3. The injector of claim 2 wherein said toothed faces of said movable members have an arcuate surface.

4. The injector of claim 3 wherein said movable members are biased toward each other and slide along and grip the rearwardly extending coupling element of a syringe plunger located between the movable members.

5. The injector of claim 1 further comprising a housing, said syringe mount being located to mount a syringe external to said housing.

6. The injector of claim 5 wherein said housing further comprises a movable arm connected to said housing and a movable face plate incorporating said syringe mount, and said injector further comprises a mechanism to facilitate translatory motion of said face plate with respect to said drive ram.

7. The injector of claim 6 wherein said mechanism to facilitate translatory motion of said face plate is a lever having locked and unlocked positions, wherein motion of said lever to said locked position causes attachment of a syringe to said injector housing by translating said rearward facing coupling element of said syringe plunger against a coupling mechanism of said plunger drive ram to facilitate cooperative movement of said syringe plunger and said plunger drive ram to inject fluids into said animal subject.

8. The injector of claim 7 wherein movement of said lever from said locked to said unlocked position results in translatory movement of said face plate along a plane perpendicular to the axis of said plunger drive ram to disengage said rearward facing coupling element of said syringe plunger from a coupling mechanism of said plunger drive ram.

9. The injector of claim 1 further comprising a syringe for mounting to an injector for injecting fluids into an animal subject, said syringe comprising:
   a cylindrical barrel;
   a plunger snugly slidable in said cylindrical barrel, said plunger having a rearwardly facing drive ram engaging coupling element thereon in the shape of a rearwardly facing extension exhibiting no discontinuity in its transverse cross-sections along the portion of said extension gripped by said coupling mechanism; and
   a discharge tip in fluid communication with said cylindrical barrel.

10. The injector of claim 9 wherein said extension is knurled.

11. The injector of claim 9 wherein said injector comprises injector mating sections positioned about said syringe mounting, and said syringe comprises syringe mating sections positioned in a plane perpendicular to the axis of the body of the syringe and arranged so as to align with the injector mating sections.

\* \* \* \* \*